United States Patent
Park et al.

(10) Patent No.: US 9,395,430 B2
(45) Date of Patent: Jul. 19, 2016

(54) METHOD OF GENERATING MAGNETIC RESONANCE IMAGE, METHOD OF ACQUIRING PHASE INFORMATION OF PHASE CONTRAST IMAGE, METHOD OF ACQUIRING PHASE INFORMATION OF SUSCEPTIBILITY WEIGHTED IMAGE, AND APPARATUS FOR GENERATING MAGNETIC RESONANCE IMAGE

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Hyun-wook Park, Daejeon (KR); Jae-moon Jo, Seongnam-si (KR); Dong-chan Kim, Daejeon (KR); Ye-ji Han, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

( * ) Notice: Subject to any disclaimer, the term of this patent is extended or adjusted under 35 U.S.C. 154(b) by 126 days.

(21) Appl. No.: 14/487,514

(22) Filed: Sep. 16, 2014

(65) Prior Publication Data

US 2015/0078644 A1 Mar. 19, 2015

(30) Foreign Application Priority Data

Sep. 16, 2013 (KR) .................. 10-2013-0111181

(51) Int. Cl.
*G06K 9/52* (2006.01)
*G01R 33/561* (2006.01)
(Continued)

(52) U.S. Cl.
CPC ............ *G01R 33/5611* (2013.01); *A61B 5/055* (2013.01); *G01R 33/5608* (2013.01); *G01R 33/56536* (2013.01)

(58) Field of Classification Search
None
See application file for complete search history.

(56) References Cited

U.S. PATENT DOCUMENTS

| | | | |
|---|---|---|---|
| 6,841,998 B1 | 1/2005 | Griswold | |
| 2013/0099784 A1* | 4/2013 | Setsompop | ............ G01R 33/54 324/309 |

(Continued)

FOREIGN PATENT DOCUMENTS

| | | |
|---|---|---|
| JP | 2004-216185 A | 8/2004 |
| KR | 2004-216185 A | 8/2004 |

OTHER PUBLICATIONS

Communication dated Feb. 17, 2015 issued by the Korean Intellectual Property Office in counterpart Korean Patent Application No. 10-2013-0111181.

(Continued)

*Primary Examiner* — Stephen R Koziol
*Assistant Examiner* — Delomia L Gilliard
(74) *Attorney, Agent, or Firm* — Sughrue Mion, PLLC

(57) ABSTRACT

Disclosed are a magnetic resonance (MR) image generating method and apparatus that perform imaging on an MR image by using a radio frequency (RF) multi-coil which includes a plurality of channel coils. The MR image generating method includes generating a plurality of pieces of K-space completion data which respectively correspond to the plurality of channel coils and converting the plurality of pieces of K-space completion data to a frequency domain in order to generate a plurality of pieces of image data, combining the plurality of pieces of image data in order to acquire an MR image, and acquiring phase information which relates to the MR image based on the plurality of pieces of image data and the plurality of pieces of K-space completion data.

19 Claims, 8 Drawing Sheets

(51) Int. Cl.
*A61B 5/055* (2006.01)
*G01R 33/56* (2006.01)
*G01R 33/565* (2006.01)

(56) References Cited

U.S. PATENT DOCUMENTS

2013/0207652 A1* 8/2013 Weller ............... G01R 33/5611
 324/309
2015/0137811 A1* 5/2015 Muftuler ............... G01R 33/34
 324/309

OTHER PUBLICATIONS

Griswold, et al., "Generalized Autocalibrating Partially Parallel Acquisitions (GRAPPA)", Magnetic Resonance in Medicine, Jun. 2002, pp. 1202-1210, vol. 47, Issue 6.

Lupo, et al., "GRAPPA-based susceptibility-weighted imaging of normal volunteers and patients with brain tumor at 7 T☆", ScienceDirect, Magnetic Resonance Imaging, May 2009 (Epub Sep. 26 2008), pp. 480-488, vol. 27, Elsevier.

* cited by examiner

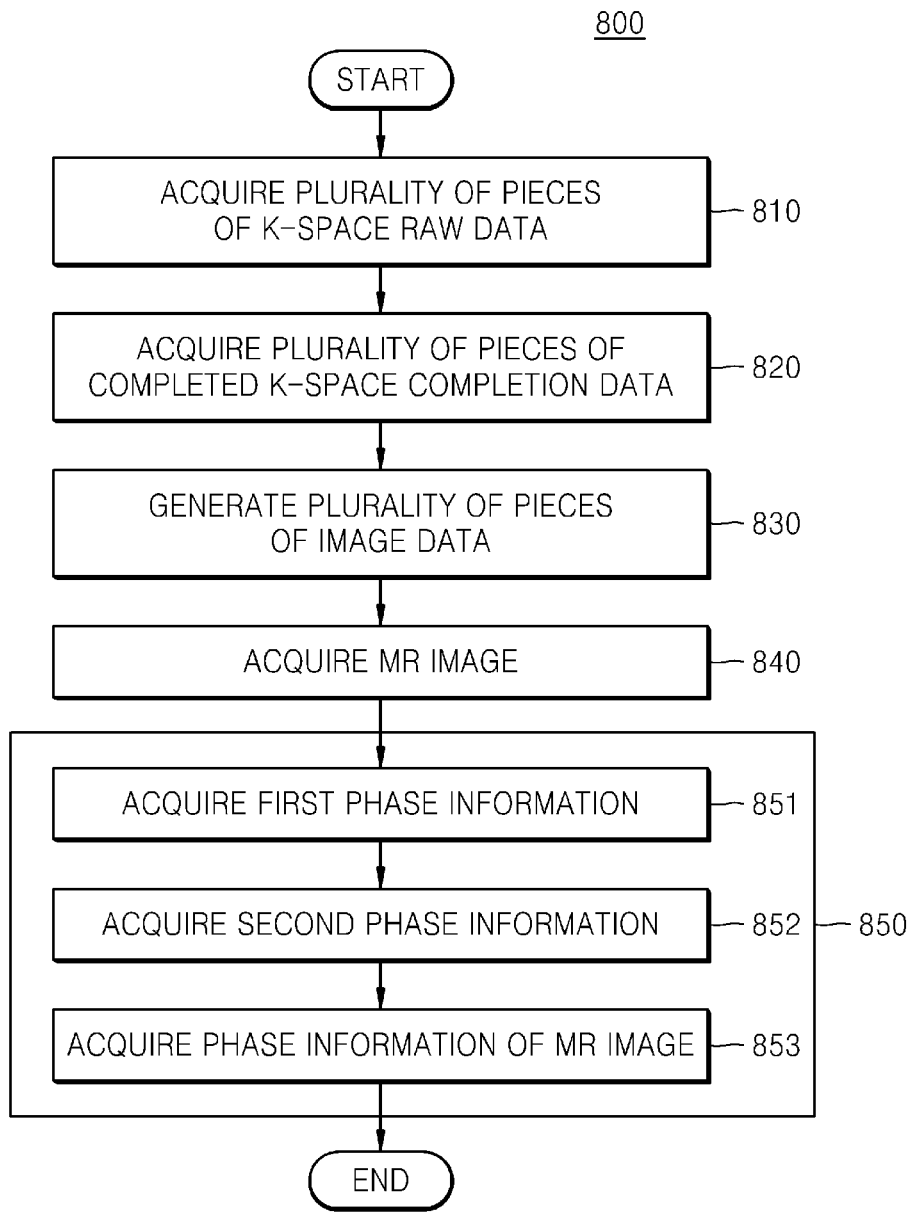

METHOD OF GENERATING MAGNETIC RESONANCE IMAGE, METHOD OF ACQUIRING PHASE INFORMATION OF PHASE CONTRAST IMAGE, METHOD OF ACQUIRING PHASE INFORMATION OF SUSCEPTIBILITY WEIGHTED IMAGE, AND APPARATUS FOR GENERATING MAGNETIC RESONANCE IMAGE

CROSS-REFERENCE TO RELATED APPLICATION

This application claims priority from Korean Patent Application No. 10-2013-0111181, filed on Sep. 16, 2013, in the Korean Intellectual Property Office, the disclosure of which is incorporated herein by reference in its entirety.

BACKGROUND

1. Field

One or more exemplary embodiments relate to a method of generating a magnetic resonance image, a method of acquiring phase information of a phase contrast image, a method of acquiring phase information of a susceptibility weighted image, and an apparatus for generating a magnetic resonance image, and more particularly, to a method of generating a magnetic resonance image, a method of acquiring phase information of a phase contrast image, a method of acquiring phase information of a susceptibility weighted image, and an apparatus for generating a magnetic resonance image, which use a generalized auto-calibrating partially parallel acquisition (GRAPPA) technique.

2. Description of the Related Art

Magnetic resonance imaging (MRI) apparatuses are apparatuses that photograph an object by using a magnetic field. MRI apparatuses three-dimensionally show lumbar discs, joints, and nerve ligaments, in addition to bones, at a desired angle, and thus are being widely used for obtaining an accurate diagnosis of a disease.

MRI apparatuses acquire a magnetic resonance (MR) signal, reconfigure the acquired MR signal into an image, and output the image. In detail, MRI apparatuses acquire the MR signal by using radio frequency (RF) coils, a permanent magnet, and a gradient coil. When the MR signal is acquired, an unmeasured signal is generated at a junction portion between the RF coils. When generating a final MR image, a defect and noise may occur due to the unmeasured signal. Further, while K-space data acquired by the RF coils is being restored to an MR image, noise of the K-space data may be amplified.

Therefore, in order to finally output an MR image from which the above-described defect and noise are removed, it is required to correct the acquired MR signal via image processing, such as, for example, calibration.

An example of an MRI method for processing an acquired MR signal includes a K-space-based GRAPPA technique.

The GRAPPA technique, a K-space-based imaging method, performs self-calibration to calculate spatial correlations and/or convolution kernels between a calibration signal and a measured source signal which is adjacent thereto, estimates an unmeasured signal, and uses the estimated signal.

In detail, the GRAPPA technique restores unobtained K-space lines by channel by using a measured signal that includes undersampled data and an additional auto-calibration signal (ACS) line. Furthermore, the GRAPPA technique converts K-space data (which is restored by multichannel coils) into an image, and combines images of respective channels in a magnitude domain in order to acquire a final image. By combining the images of the respective channels in the magnitude domain, a quality of an image is prevented from being degraded by a phase difference due to interference between the channels.

The GRAPPA technique processes K-space data in parallel by coils which respectively correspond to the multichannel coils. Therefore, a time taken in acquiring a final image is shortened.

However, since the final image acquired by the GRAPPA technique is obtained via the combination in the magnitude domain, the final image includes only magnitude information, and does not include phase information.

Since the final image acquired by the GRAPPA technique does not include the phase information, the final image cannot be applied to an imaging technique which uses phase information, such as, for example, a phase contrast imaging (PCI) technique and a susceptibility weighted imaging (SWI) technique.

Due to this, it is required to provide an MR image generating method and apparatus that shorten a time taken in acquiring an MR image in a similar manner as via the GRAPPA technique, and acquire phase information of a final image.

SUMMARY

One or more exemplary embodiments include a method of generating a magnetic resonance image, a method of acquiring phase information of a phase contrast image, a method of acquiring phase information of a susceptibility weighted image, and an apparatus for generating a magnetic resonance image, and more particularly, to a method of generating a magnetic resonance image, a method of acquiring phase information of a phase contrast image, a method of acquiring phase information of a susceptibility weighted image, and an apparatus for generating a magnetic resonance image, which shorten a time taken in acquiring an MR image and acquire phase information of a final MR image.

Additional aspects will be set forth in part in the description which follows and, in part, will be apparent from the description, or may be learned by practice of the presented exemplary embodiments.

According to one or more exemplary embodiments, provided is a magnetic resonance (MR) image generating method for acquiring an MR image by using a radio frequency (RF) multi-coil which includes a plurality of channel coils, the MR image generating method including: generating a plurality of pieces of K-space completion data which respectively correspond to the plurality of channel coils, and converting the plurality of pieces of K-space completion data to a frequency domain in order to generate a plurality of pieces of image data; combining the plurality of pieces of image data in order to acquire an MR image; and acquiring phase information which relates to the MR image based on at least one of a plurality of pieces of first phase information and a plurality of pieces of second phase information, wherein each of the plurality of pieces of first phase information is channel-specific and is acquired from and corresponds to a respective one of the plurality of pieces of image data, and wherein each of the plurality of pieces of second phase information is channel-specific and is acquired from and corresponds to a respective one of the plurality of pieces of K-space completion data.

Each of the plurality of pieces of the first phase information may include a respective phase value of a center pixel in the corresponding one of the plurality of pieces of image data.

Each of the plurality of pieces of the second phase information may include a respective phase value at a point in which a signal value of the corresponding one of the plurality of pieces of K-space completion data becomes a maximum value.

The acquiring the phase information may include acquiring, as the phase information of the MR image, an average value of the plurality of pieces of first phase information.

The acquiring the phase information may include acquiring, as the phase information of the MR image, an average value of the plurality of pieces of second phase information when the RF multi-coil includes a dome-type RF multi-coil.

The acquiring the phase information may include: acquiring the second phase information on a first channel in which a signal-to-noise ratio (SNR) in a center region of the image data is equal to or less than a predetermined value; acquiring the first phase information on a second channel in which the SNR in the center region of the data is greater than the predetermined value; and acquiring the phase information which relates to the MR image based on the acquired first phase information and the acquired second phase information.

The generating the plurality of pieces of image data may include: acquiring a plurality of pieces of K-space raw data which respectively correspond to the plurality of channel coils; performing an auto-calibration on the acquired plurality of pieces of K-space raw data in order to generate the plurality of pieces of K-space completion data; and performing a fast Fourier transform (FFT) on the generated plurality of pieces of K-space completion data in order to generate the plurality of pieces of image data.

The plurality of pieces of K-space raw data may include a plurality of pieces of under-sampled K-space data which respectively correspond to the plurality of channel coils, and the generating the plurality of pieces of K-space completion data may include: estimating data of an auto-calibration line by using line data which is included in the under-sampled K-space data; estimating line data which is not included in the under-sampled K-space data, based on the acquired line data and the data of the auto-calibration line; and generating the K-space completion data based on the estimated line data and the acquired line data.

The acquiring the MR image may include calculating a sum of squares which respectively correspond to the plurality of pieces of image data.

According to one or more exemplary embodiments, a method for acquiring phase information of a phase contrast image (PCI) includes: generating a plurality of pieces of K-space completion data which respectively correspond to a plurality of channel coils, and converting the plurality of pieces of K-space completion data to a frequency domain in order to generate a plurality of pieces of image data; and acquiring the phase information which relates to the PCI based on at least one of a plurality of pieces of first phase information and a plurality of pieces of second phase information, wherein each of the plurality of pieces of first phase information is channel-specific and is acquired from and corresponds to a respective one of the plurality of pieces of image data, and wherein each of the plurality of pieces of second phase information is channel-specific and is acquired from and corresponds to a respective one of the plurality of pieces of K-space completion data.

According to one or more exemplary embodiments, a method for acquiring phase information which relates to a susceptibility weighted image (SWI) includes: generating a plurality of pieces of K-space completion data which respectively correspond to a plurality of channel coils, and converting the plurality of pieces of K-space completion data to a frequency domain in order to generate a plurality of pieces of image data; and acquiring the phase information which relates to the SWI based on at least one of a plurality of pieces of first phase information and a plurality of pieces of second phase information wherein each of the plurality of pieces of first phase information is channel-specific and is acquired from and corresponds to a respective one of the plurality of pieces of image data, and wherein each of the plurality of pieces of second phase information is channel-specific and is acquired from and corresponds to a respective one of the plurality of pieces of K-space completion data.

According to one or more exemplary embodiments, provided is a magnetic image (MR) image generating apparatus for acquiring an MR image by using a radio frequency (RF) multi-coil which includes a plurality of channel coils, the MR image generating apparatus including: an image processor configured to generate a plurality of pieces of K-space completion data which respectively correspond to the plurality of channel coils, to convert the plurality of pieces of K-space completion data to a frequency domain in order to generate a plurality of pieces of image data, and to combine the generated plurality of pieces of image data in order to acquire the MR image; and a phase information acquirer configured to acquire phase information which relates to the MR image based on at least one of a plurality of pieces of first phase information and a plurality of pieces of second phase information, wherein each of the plurality of pieces of first phase information is channel-specific and is acquired from and corresponds to a respective one of the plurality of pieces of image data, and wherein each of the plurality of pieces of second phase information is channel-specific and is acquired from and corresponds to a respective one of the plurality of pieces of K-space completion data.

BRIEF DESCRIPTION OF THE DRAWINGS

These and/or other aspects will become apparent and more readily appreciated from the following description of exemplary embodiments, taken in conjunction with the accompanying drawings in which:

FIG. 8 is a flowchart of an MR image generating method, according to another exemplary embodiment.

DETAILED DESCRIPTION

Figure 1:
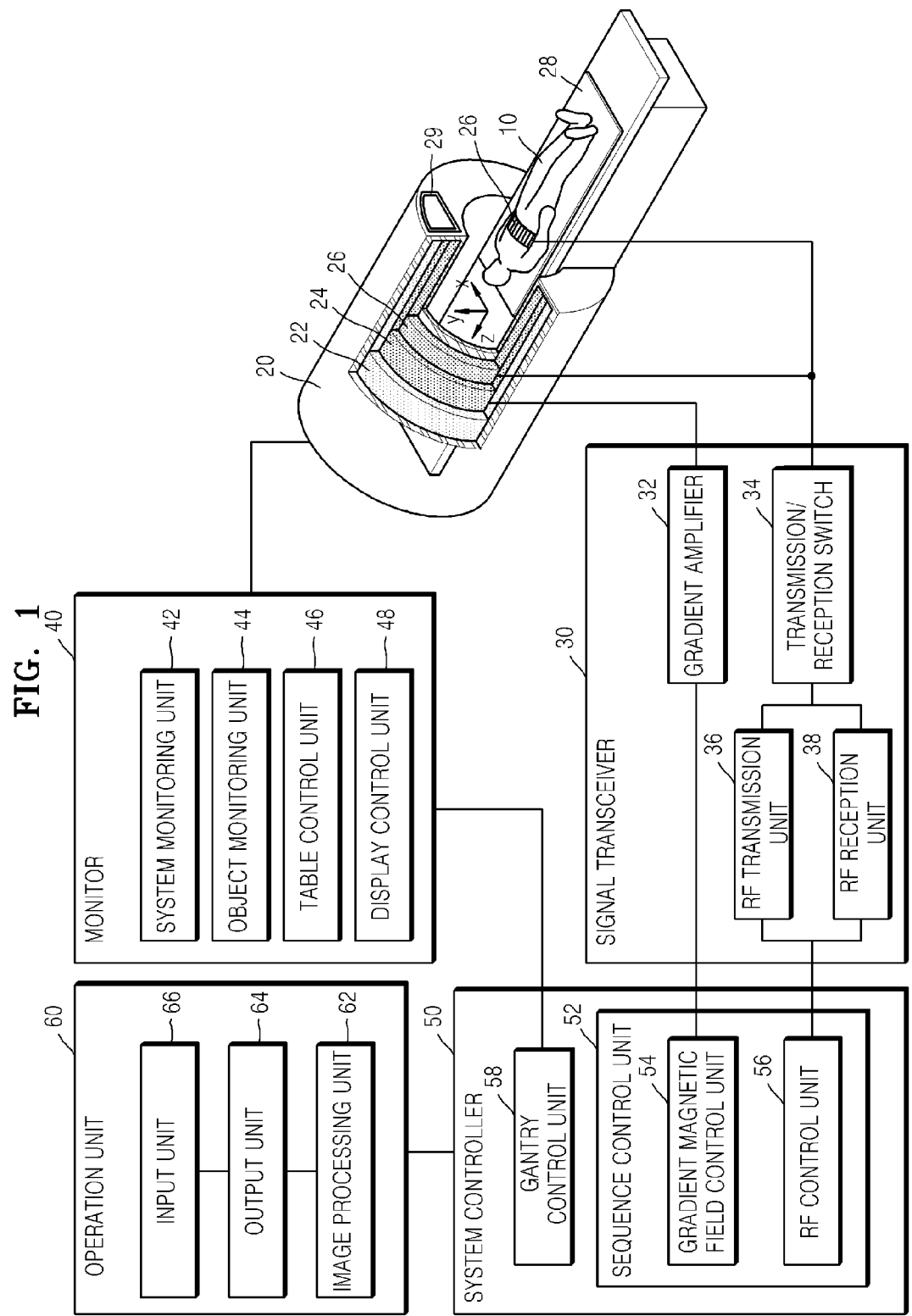
FIG. 1 is a schematic diagram illustrating a general MRI system.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. Expressions such as "at least one of," when preceding a list of elements, modify the entire list of elements and do not modify the individual elements of the list.

The advantages, features and aspects of the present disclosure will become apparent from the following description of the exemplary embodiments with reference to the accompanying drawings, which is set forth hereinafter. The present inventive concept may, however, be embodied in different forms and should not be construed as limited to the exemplary embodiments set forth herein. Rather, these exemplary embodiments are provided so that this disclosure will be thorough and complete, and will fully convey the scope of the present disclosure to those skilled in the art.

Terms used herein will be briefly described, and the exemplary embodiments will be described in detail.

Terms used in the present disclosure have been selected as general terms which are widely used at present, in consideration of the functions of the exemplary embodiments, but may be altered according to the intent of an operator skilled in the art, conventional practice, or introduction of new technology. Also, if there is a term which is arbitrarily selected by the applicant in a specific case, in which case a meaning of the term will be described in detail in a corresponding description portion of the present disclosure. Therefore, the terms should be defined on the basis of the entire content of this specification instead of a simple name of each of the terms.

In this disclosure below, when it is described that one comprises (or includes) or in this disclosure below, when it is described that one comprises (or includes or has) some elements, it should be understood that it may comprise (or include or has) only those elements, or it may comprise (or include or have) other elements as well as those elements if there is no specific limitation. The term "module", as used herein, means, but is not limited to, a software or hardware component, such as a Field Programmable Gate Array (FPGA) or an Application Specific Integrated Circuit (ASIC), which performs certain tasks. A module may advantageously be configured to reside in the addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Exemplary embodiments that are capable of being easily embodied by those skilled in the art will now be described in detail with reference to the accompanying drawings. In the accompanying drawings, a portion irrelevant to a description of one or more exemplary embodiments will be omitted for clarity.

The term "image" used herein may denote multi-dimensional data composed of discrete image factors (for example, pixels in a two-dimensional (2D) image and pixels in a three-dimensional (3D) image). For example, an image may include a medical image of an object which is acquired by an X-ray apparatus, a CT apparatus, a magnetic resonance imaging (MRI) apparatus, an ultrasonic apparatus, and/or another medical image photographing apparatus.

Moreover, the term "object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume that is very close to a density of organisms and an effective atomic number, and may include a spherical phantom having a temper similar to a human body.

Moreover, the term "user" used herein may include a medical expert, and may be a doctor, a nurse, a medical technologist, a medical image expert, or the like, or may be an engineer repairing a medical apparatus. However, the user is not limited thereto.

Moreover, the term "magnetic resonance imaging (MRI)" used herein denotes an image of an object which is obtained by using the nuclear magnetic resonance principle.

Moreover, the term "pulse sequence" used herein denotes a continuation of a repeatedly applied signal in an MRI apparatus. The pulse sequence may include a time parameter of a radio frequency (RF) pulse, for example, a repetition time (TR) and a time to echo (TE).

An MRI system is equipment that expresses an intensity of a magnetic resonance (MR) signal to an RF signal (which is generated in a magnetic field having a specific intensity) as a contrast, and thus obtains an image of a tomographic part of an object. For example, an object is laid in a strong magnetic field, and when the RF signal, which only resonates a specific atomic nucleus (for example, a hydrogen atomic nucleus or the like), is momentarily irradiated on the object and then stopped, an MR signal is emitted from the specific atomic nucleus, in which case the MRI system receives the MR signal in order to obtain an MR image. The MR signal denotes an RF signal emitted from the object. A level of the MR signal may be determined based on a concentration of a specific atom (for example, hydrogen or the like) of the object, a relaxation time $T_1$, a relaxation time $T_2$, and/or a blood flow.

An MRI system has different features from those of other imaging apparatuses. Unlike imaging apparatuses such as CT apparatuses in which acquisition of an image is dependent on a direction of detection hardware, the MRI system may acquire a two-dimensional (2D) image and/or a three-dimensional (3D) volume image which is oriented with respect to an arbitrary point. Also, unlike CT apparatuses, X-ray apparatuses, position emission tomography (PET) apparatuses, and SPECT apparatuses, the MRI system may acquire an image having a high soft tissue without exposing radiation to an object and an examinee, and thus acquire a neurological image, an intravascular image, a musculoskeletal image, and/or an oncologic image which need a clear description of an abnormal tissue.

FIG. 1 is a schematic diagram illustrating a general MRI system. Referring to FIG. 1, the general MRI system may include a gantry 20, a signal transceiver 30, a monitor 40, a system controller 50, and an operation unit (also referred to herein as an "operator" and/or as an "operation device") 60.

The gantry 20 prevents an electromagnetic wave, generated by a main magnet 22, a gradient coil 24, and a radio frequency (RF) coil 26, from being emitted to the outside. A static electromagnetic field and a gradient magnetic field are generated at a bore of the gantry 20, and an RF signal is irradiated toward an object 10.

The main magnet 22, the gradient coil 24, and the RF coil 26 may be disposed along a certain direction of the gantry 20. The certain direction may include a coaxial cylinder direction. The object 10 may be located on a table 28, which is insertable into a cylinder along a horizontal axis of the cylinder.

The main magnet 22 generates a static electromagnetic field or a static magnetic field for aligning magnetic dipole moments of atomic nuclei of the object 10 in a constant direction. As the magnetic field generated by the main magnet 22 becomes stronger and more uniform, a relatively precise and accurate MR image of the object 10 is acquired.

The gradient coil 24 includes X, Y, and Z coils that respectively generate gradient magnetic fields in X-axis, Y-axis, and Z-axis directions that are orthogonal to each other. The gradient coil 24 may induce different resonance frequencies for each part of the object 10, and provide position information of each part of the object 10.

The RF coil 26 may irradiate an RF signal on a patient as the object 10, and receive an MR signal which is emitted from the patient. In particular, the RF coil 26 may transmit an RF signal, which has a same frequency as that of a precessional motion, to the patient toward an atomic nucleus which is performing the precessional motion, stop the transmission of the RF signal, and receive an MR signal which is emitted from the patient.

For example, in order to excite a specific atomic nucleus from a low energy level to a high energy level, the RF coil 26 may generate an electromagnetic wave signal (for example, an RF signal) which has an RF corresponding to a type of the specific atomic nucleus, and apply the electromagnetic wave signal to the object 10. When the electromagnetic wave signal generated by the RF coil 26 is applied to a specific atomic nucleus, the specific atomic nucleus may be excited from a low energy level to a high energy level. Then, when the electromagnetic wave signal generated by the RF coil 26 dissipates, an energy level of the specific atomic nucleus to which the electromagnetic wave is applied may be changed from the high energy level to the low energy level, and an electromagnetic wave having a Larmor frequency may be emitted. The RF coil 26 may receive an electromagnetic wave signal emitted from internal atomic nuclei of the object 10.

The RF coil 26 may be implemented as a single RF transmission/reception coil that has a function of generating an electromagnetic wave which has an RF corresponding to a type of atomic nucleus and a function of receiving an electromagnetic wave which is emitted from the atomic nucleus. Alternatively, the RF coil 26 may be configured with a transmission RF coil that has the function of generating an electromagnetic wave which has an RF corresponding to a type of atomic nucleus and a reception RF coil that has a function of receiving an electromagnetic wave which is emitted from the atomic nucleus.

Moreover, the RF coil 26 may be fixed to the gantry 20, or may be detachably attached to the gantry 20. The attachable/detachable RF coil 26 may include a plurality of RF coils including any one or more of a head RF coil, a chest RF coil, a leg RF coil, a neck RF coil, a shoulder RF coil, a wrist RF coil, and/or an ankle RF coil for some parts of an object, depending on a diagnosis part of the object.

Moreover, the RF coil 26 may communicate with an external device in a wired manner and/or a wireless manner, and may perform dual tune communication based on a communication frequency band.

Moreover, the RF coil 26 may include any one or more of a birdcage coil, a surface coil, and a TEM coil, depending on a shape and structure of a coil.

Moreover, the RF coil 26 may include any one or more of a transmission dedicated coil, a reception dedicated coil, and a transmission/reception coil, depending on an RF signal transmission/reception method.

Moreover, the RF coil 26 may include RF coils which correspond to any one or more of various numbers of channels, such as 16 channel, 3 channel, 72 channel, and 144 channel.

Hereinafter, as an example, a case will be described in which the RF coil 26 is an RF multi-coil that includes N number of coils which respectively correspond to a plurality of channels, namely, first to Nth channels. Here, the RF multi coil may be referred to as a multichannel RF coil.

The gantry 20 may further include a display 29 which is disposed outside the gantry 20 and a display (not shown) which is disposed inside the gantry 20. A user may provide certain information to the object 10 by using the displays which are respectively disposed inside and outside the gantry 20.

The signal transceiver 30 may control a gradient magnetic field which is generated inside (i.e., within the bore) the gantry 20, and may control a transmission/reception of an RF signal and an MR signal, according to a certain MR sequence.

The signal transceiver 30 may include a gradient amplifier 32, a transmission/reception switch 34, an RF transmission unit (also referred to herein as an "RF transmitter") 36, and an RF reception unit (also referred to herein as an "RF receiver") 38.

The gradient amplifier 32 may drive the gradient coil 24 which is included in the gantry 20, and may supply a pulse signal, used to generate a gradient magnetic field, to the gradient coil 24 according to control by a gradient magnetic field control unit (also referred to herein as a "gradient magnetic field controller") 54. Gradient magnetic fields in the X-axis, Y-axis, and Z-axis directions may be synthesized by controlling the pulse signal which is supplied from the gradient amplifier 32 to the gradient coil 24.

The RF transmission unit 36 and the RF reception unit 38 may drive the RF coil 26. The RF transmission unit 36 may supply an RF pulse having a Larmor frequency to the RF coil 26, and the RF reception unit 38 may receive an MR signal received by the RF coil 26.

The transmission/reception switch 34 may adjust a transmission/reception direction of each of the RF and MR signals. For example, in a transmission mode, the transmission/reception switch 34 may irradiate the RF signal toward the object 10 via the RF coil 26, and in a reception mode, the transmission/reception switch 34 may receive the MR signal from the object 10 via the RF coil 26. The transmission/reception switch 34 may be controlled by a control signal which is received from an RF control unit (also referred to herein as an "RF controller") 56.

The monitor 40 may monitor and/or control the gantry 20 and/or elements included in the gantry 20. The monitor 40 may include a system monitoring unit (also referred to herein as a "system monitor") 42, an object monitoring unit (also referred to herein as an "object monitor") 44, a table control unit (also referred to herein as a "table controller") 46, and a display control unit (also referred to herein as a "display controller") 48.

The system monitoring unit 42 may monitor and/or control any one or more of a state of a static magnetic field, a state of a gradient magnetic field, a state of an RF signal, a state of an RF coil, a state of a table, a state of an element that measures body information of an object, a power supply state, a state of a heat exchanger, a state of a compressor, etc.

The object monitoring unit 44 monitors a state of the object 10. In particular, the object monitoring unit 44 may include any one or more of a camera for observing a movement or position of the object 10, a breath measurer for measuring a breath of the object 10, an electrocardiogram (ECG) measurer for measuring an ECG of the object 10, and/or a body temperature measurer for measuring a body temperature of the object 10.

The table control unit 46 controls a movement of the table 28 with the object 10 located thereon. The table control unit 46 may control the movement of the table 28 based on sequence control by the system controller 50. For example, in capturing a moving image of an object, the table control unit 46 may continuously or intermittently move the table 28 based on the sequence control by the system controller 50, and thus photograph the object 10 at a view greater than a field of view (FOV) of the gantry 20.

The display control unit 48 controls the displays which are respectively disposed outside and inside the gantry 20. In particular, the display control unit 48 may control turn-on/off of the displays disposed outside and inside the gantry 20, and/or control a screen displayed by each of the displays. Also, when a speaker is disposed inside or outside the gantry 20, the display control unit 48 may control turn-on/off of the speaker and/or sound outputted by the speaker.

The system controller 50 may include a sequence control unit 52 that controls a sequence of signals generated in the gantry 20 and a gantry control unit 58 that controls the gantry 20 and elements mounted on the gantry 20.

The sequence control unit 52 may include the gradient magnetic field control unit 54 that controls the gradient amplifier 32, and the RF control unit 56 that controls the RF transmission unit 36, the RF reception unit 38, and the transmission/reception switch 34. The sequence control unit 52 may control the gradient amplifier 32, the RF transmission unit 36, the RF reception unit 38, and the transmission/reception switch 34 based on a pulse sequence received from the operation unit 60. Here, the pulse sequence includes all information which is necessary to control the gradient amplifier 32, the RF transmission unit 36, the RF reception unit 38, and the transmission/reception switch 34, and for example, may include information which relates to an intensity of a pulse signal applied to the gradient coil 24, an application time, and an application timing.

The operation unit 60 may provide pulse sequence information to the system controller 50, and simultaneously control an overall operation of the MRI apparatus.

The operation unit 60 may include an image processing unit (also referred to herein as an "image processor") 62 that processes the MR signal received from the RF reception unit 38, an output unit (also referred to herein as an "output device") 64, and an input unit (also referred to herein as an "input device") 66.

The image processing unit 62 may process the MR signal which is received from the RF reception unit 38 in order to generate an MRI image that includes MRI image data relating to the object 10.

The image processing unit 62 may perform any one or more of various signal processing operations, such as amplification, frequency conversion, phase detection, low-frequency amplification, and filtering, on the MR signal which is received by the RF reception unit 38.

The image processing unit 62, for example, may arrange digital data in a k-space, and perform a 2D or 3D Fourier transform on the digital data in order to reconfigure the digital data into image data.

Moreover, depending on the case, the image processing unit 62 may perform a synthesis processing and/or a differential operation processing on the image data. The synthesis processing may include an addition processing and a maximum intensity projection (MIP) processing on a pixel. Also, the image processing unit 62 may store image data, on which the synthesis processing and/or differential operation processing has been performed, in addition to the reconfigured image data, in a memory (not shown) or an external server.

Moreover, the image processing unit 62 may perform various signal processing functions in parallel on the MR signal. For example, the image processing unit 62 may perform, in parallel, signal processing on a plurality of MR signals which are received by a multi-channel RF coil in order to reconfigure the plurality of MR signals into image data.

The output unit 64 may output the image data generated and/or the image data reconfigured by the image processing unit 62 to a user. Also, the output unit 64 may output information (which is necessary for the user to manipulate the MRI apparatus) such as a user interface (UI), user information, or object information, in addition to the MRI image. The output unit 64 may include any one or more of a speaker, a printer, a CRT display, an LCD, a PDP, an OLED display, an FED, an LED display, a VFD, a DLP display, a PFD, a 3D display, a transparent display, etc., and may include any one or more of various output devices within a scope which will be apparent to those skilled in the art.

The user may input any one or more of object information, parameter information, a scanning condition, a pulse sequence, information on image synthesis or differential operation, etc. by using the input unit 66. The input unit 66 may include any one or more of a keyboard, a mouse, a trackball, a voice recognizer, a gesture recognizer, a touch pad, a touch screen, etc., and may include any one or more of various input devices within a scope which will be apparent to those skilled in the art.

FIG. 1 illustrates the signal transceiver 30, the monitor 40, the system controller 50, and the operation unit 60 as separate elements. However, those skilled in the art will understand that respective functions performed by the signal transceiver 30, the monitor 40, the system controller 50, and the operation unit 60 may be performed by different elements. For example, it has been described above that the image processing unit 62 converts the MR signal received by the RF reception unit 38 into a digital signal, but the conversion from the MR signal to the digital signal may be performed directly by the RF reception unit 38 and/or by the RF coil 26.

The gantry 20, the signal transceiver 30, the monitor 40, the system controller 50, and the operation unit 60 may be connected to each other in a wired manner and/or a wireless manner. When they are connected in a wired manner, an element for synchronizing a clock therebetween may be further provided. Communication between the gantry 20, the signal transceiver 30, the monitor 40, the system controller 50, and the operation unit 60 may use a high-speed digital interface, such as any one or more of a low voltage differential signaling (LVDS), asynchronous serial communication such as a universal asynchronous receiver transmitter (UART), a low-delay network protocol such as synchronous serial communication or a can area network (CAN), and/or optical communication, and may use any one or more of various communication schemes within a scope which will be apparent to those skilled in the art.

Figure 2:
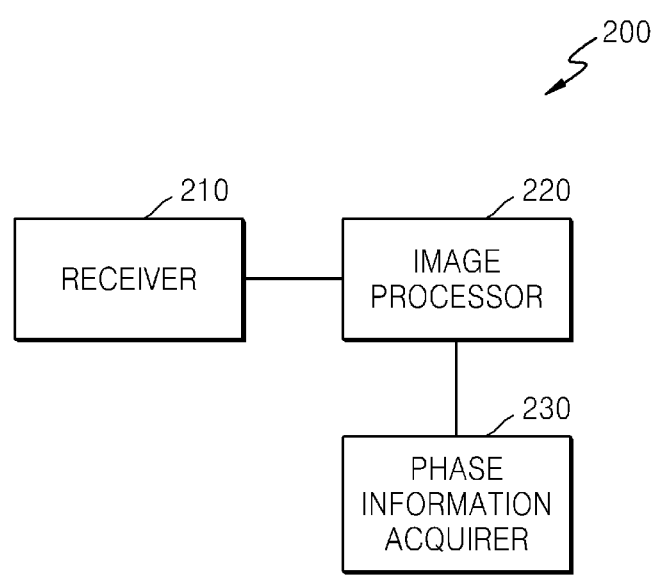
FIG. 2 is a diagram illustrating an MR image generating apparatus, according to an exemplary embodiment.

FIG. 2 is a diagram illustrating an MR image generating apparatus 200, according to an exemplary embodiment.

Referring to FIG. 2, the MR image generating apparatus 200 according to an exemplary embodiment includes an image processor 220 and a phase information acquirer 230. Also, the MR image generating apparatus 200 may further include a receiver 210. In the MR image generating apparatus 200, the image processor 220 is the same element as the image processing unit 62 of FIG. 1, and thus, the same descriptions provided with regard to FIG. 1 are not repeated.

The MR image generating apparatus 200 is an apparatus that performs imaging on an MR image by using an RF multi-coil which includes a plurality of channel coils.

In particular, the MR image generating apparatus 200 receives a plurality of pieces of data which have been acquired by the RF multi-coil including the plurality of coils, and generates an MR image by using the received plurality of pieces of data. Here, the plurality of pieces of data received by the MR image generating apparatus 200 may include raw data which is generated in a K-space. In detail, the raw data is a signal that is generated by arranging RF signals, which are respectively received by channel-specific coils which are included in the RF multi-coil, in the K-space.

The receiver 210 receives an RF signal received by the RF reception unit 38. Here, the RF signal received by the receiver 210 includes K-space data received by each of a plurality of channel coils included in the RF coil 26. Here, the RF coil 26 is an RF multi-coil which includes the plurality of coils which respectively correspond to the plurality of channel coils. In detail, the RF coil 26 includes first to nth channel coils, each of which receives the RF signal. In this case, the RF receiving unit 38 may arrange the RF signals, received by the RF coil 26, in the K-space to generate n pieces of raw data, and transfer the n pieces of raw data to the receiver 210.

Hereinafter, the RF coil 26 is referred to as an RF multi-coil.

Moreover, the receiver 210 may directly receive the RF signals received by the RF coil 26. In this case, the receiver 210 may arrange the RF signals in the K-space in order to generate the n pieces of raw data which respectively correspond to n number of channels.

Hereinafter, a signal obtained from the RF signal received by each of the n channel coils is referred to as K-space raw data. The K-space raw data is a signal upon which an auto-calibration has not been performed, and is an under-sampled signal. The K-space raw data will be described below in detail with reference to FIG. 3.

In the MR image generating apparatus 200, the receiver 210 may internally include the image processor 220. In this case, the image processor 220 may directly receive the RF signals and generate n pieces of K-space raw data based on the received RF signals, or may directly receive the n pieces of K-space raw data.

The image processor 220 drives the RF coil 26, which is the RF multi-coil including the plurality of channel coils, in order to generate a plurality of pieces of K-space completion data which respectively correspond to the plurality of channel coils. The image processor 220 converts the plurality of pieces of K-space completion data to a frequency domain in order to generate a plurality of image data, and then combines the plurality of image data in order to acquire an MR image. Here, the MR image may be a magnitude image which is generated by combining a plurality of image data in a magnitude domain. Hereinafter, the magnitude image which is generated by combining a plurality of image data, which respectively correspond to the plurality of channel coils, in a magnitude domain is referred to as an MR image.

The phase information acquirer 230 may acquire phase information which relates to an MR image based on at least one of a plurality of pieces of first phase information, which is channel-specific phase information that corresponds to and is acquired from the plurality of image data, and a plurality of pieces of second phase information, which is channel-specific phase information that corresponds to and is acquired from the plurality of pieces of K-space completion data. The first phase information and the second phase information will be described below in detail with reference to FIGS. 3, 4, 5A, 5B, 6A, and 6B.

Figure 3:
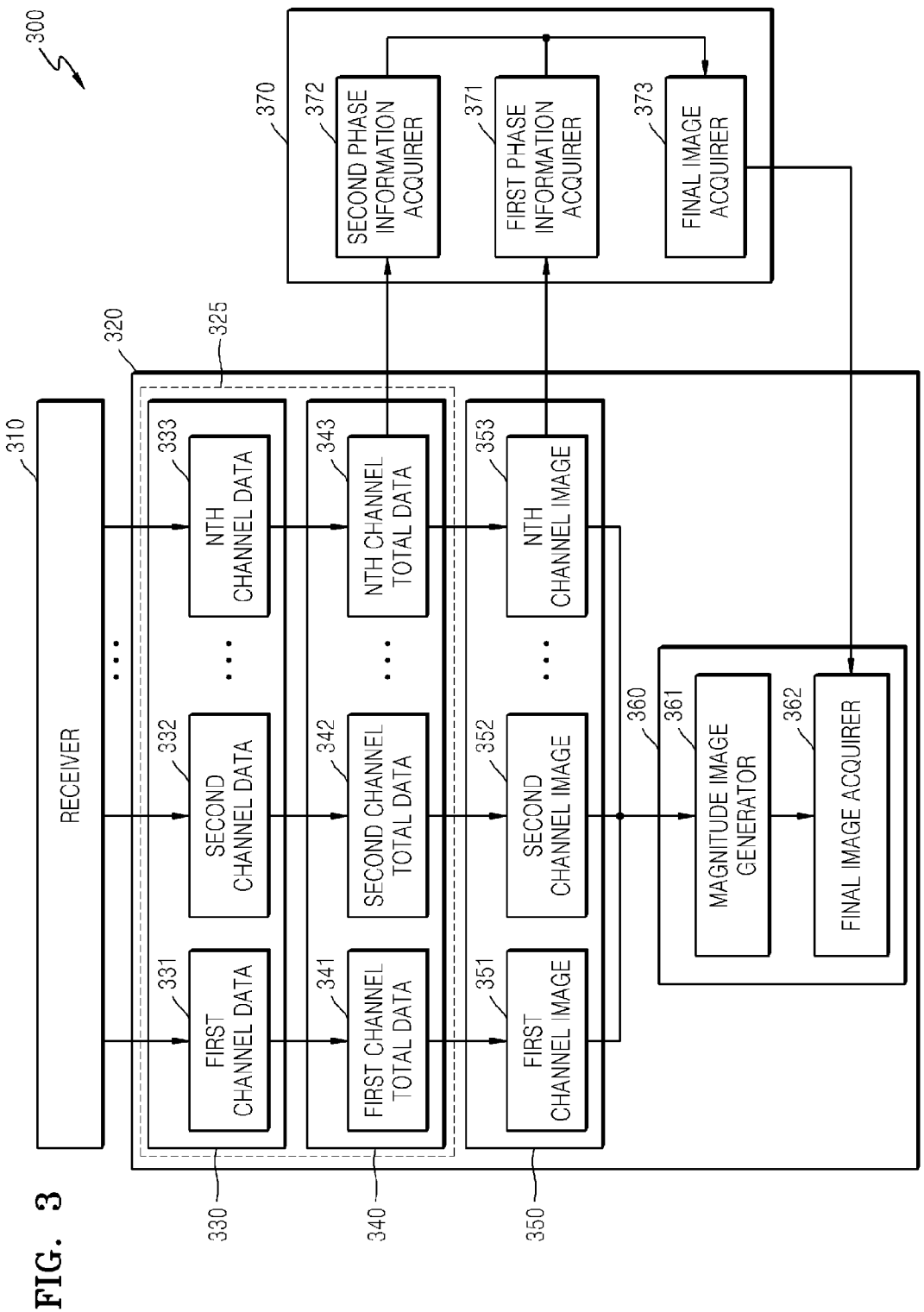
FIG. 3 is a diagram illustrating an MR image generating apparatus, according to another exemplary embodiment.

FIG. 3 is a diagram illustrating an MR image generating apparatus 300, according to another exemplary embodiment.

Referring to FIG. 3, the MR image generating apparatus 300 includes an image processor 320 and a phase information acquirer 370. Also, the MR image generating apparatus 300 may further include a receiver 310. In the MR image generating apparatus 300, the image processor 320, the phase information acquirer 370, and the receiver 310 respectively correspond to the image processor 320, the phase information acquirer 370, and the receiver 310 of FIG. 2, and thus, the same descriptions provided with regard to FIG. 1 are not repeated.

The image processor 320 may include a K-space data acquirer 325, a converter 350, and an image acquirer 360. Referring to FIG. 3, the image processor 320 processes data in parallel and in respective correspondence with a plurality of channel coils.

The K-space data acquirer 325 acquires K-space raw data from each of the plurality of channel coils, and auto-calibrates a plurality of pieces of K-space raw data in order to acquire a plurality of pieces of K-space completion data.

Here, the plurality of channel coils are N number of channel coils which respectively correspond to first to Nth channels included in an RF multi-coil that is the same as the above-described RF coil 26.

In detail, the K-space data acquirer 325 may include a K-space raw data acquirer 330 and a K-space completion data acquirer 340.

When the receiver 310 directly receives an RF signal from the RF coil 26 that is the RF multi-coil, the K-space raw data acquirer 330 may receive a plurality of the RF signals which respectively correspond to the N channel coils included in the RF coil 26, and arrange the received plurality of RF signals in the K-space in order to generate N pieces of K-space raw data which respectively correspond to the N channel coils. Also, when the receiver 310 receives the N pieces of K-space raw data, the K-space raw data acquirer 330 may receive, in parallel, the N pieces of K-space raw data which respectively correspond to the N channel coils.

The K-space raw data acquirer 330 acquires N pieces of channel data 331, 332, . . . to 333 which respectively correspond to the N channel coils.

In detail, the K-space raw data acquirer 330 acquires a plurality of pieces of under-sampled K-space data which are respectively acquired by the plurality of channel coils. Here, the N pieces of channel data 331, 332, . . . 333 are the pieces of under-sampled K-space data which respectively correspond to the first to Nth channel coils. Hereinafter, each of the N pieces of channel data 331, 332, . . . 333 is referred to as K-space raw data.

For example, the first channel data 331 is K-space raw data acquired from the first channel coil, the second channel data 332 is K-space raw data acquired from the second channel coil, and the Nth channel data 333 is K-space raw data acquired from the Nth channel coil.

The K-space completion data acquirer 340 generates a plurality of pieces of K-space completion data, which includes an image value for all lines by using the N pieces of K-space raw data transferred from the K-space raw data acquirer 330.

The MR image generating apparatus 300 may perform under-sampling for each channel in order to acquire a plurality of pieces of K-space raw data, for shortening an image acquisition time. In detail, when the total number of sample lines in a Ky direction that is a y-axis direction in the K-space is Ny, the MR image generating apparatus 300 may acquire line data in a state in which the number of lines of the acquired line data is less than Ny, and estimate unacquired line data by using an auto-calibration line. The MR image generating apparatus 300 may acquire the K-space completion data which has an image value in a total of sample lines "Ny" by using the estimated line data and the acquired line data.

For example, when desiring to reduce the image acquisition time by half, the number of sample lines in the Ky direction is set to Ny/2, and respective pieces of data for Ny/2 number of lines are acquired. The MR image generating apparatus 300 sets an auto-calibration (ACS) line data included in the acquired line data. Alternatively, the MR image generating apparatus 300 further acquires auto-calibration (ACS) line data in addition to the acquired line data in the pieces of K-space raw data. The MR image generating apparatus 300 estimates a correlation between data of the auto-calibration line data and the acquired line data, and estimates unacquired line data by applying the estimated correlation to the Ky direction. Furthermore, the MR image generating apparatus 300 restores the K-space completion data by using the estimated line data and the pieces of K-space raw data.

Hereinafter, each of N pieces of channel total data 341, 342, . . . 343 is referred to as K-space completion data. In detail, the first channel total data 341 is K-space completion data which corresponds to the first channel coil, the second channel total data 342 is K-space completion data which corresponds to the second channel coil, and the Nth channel total data 343 is K-space completion data which corresponds to the Nth channel coil.

The converter 350 performs a fast Fourier transform (FFT) on each of the N pieces of K-space completion data 341, 342, . . . 343, which respectively correspond to the N channel coils, in order to generate N pieces of image data. In detail, the converter 350 performs an FFT on the first channel total data 341 in order to generate a first channel image 351 which corresponds to the first channel coil, performs an FFT on the second channel total data 342 in order to generate a second channel image 352 which corresponds to the second channel coil, and performs an FFT on the Nth channel total data 343 in order to generate an Nth channel image 353 which corresponds to the Nth channel coil.

The image acquirer 360 may include a magnitude image generator 361 and a final image acquirer 362.

The magnitude image generator 361 calculates a sum of square values which respectively correspond to the first to Nth channel images 351 to 353 that are N pieces of image data generated by the converter 350, thereby generating an MR image including magnitude information.

The final image acquirer 362 may combine phase information, which has been acquired by the phase information acquirer 370, with the MR image generated by the magnitude image generator 361 in order to generate a final MR image (i.e., a complex image) which includes the phase information and the magnitude information.

The phase information acquirer 370 may include a first phase information acquirer 371, a second phase information acquirer 372, and a final phase acquirer 373.

The first phase information acquirer 371 acquires first phase information that is phase information which corresponds to each of the first to Nth channel images 351 to 353 which are generated by the converter 350 and which respectively correspond to the N channel coils.

The first phase information will be described below in detail with reference to FIGS. 4, 5A, and 5B.

Figure 4:
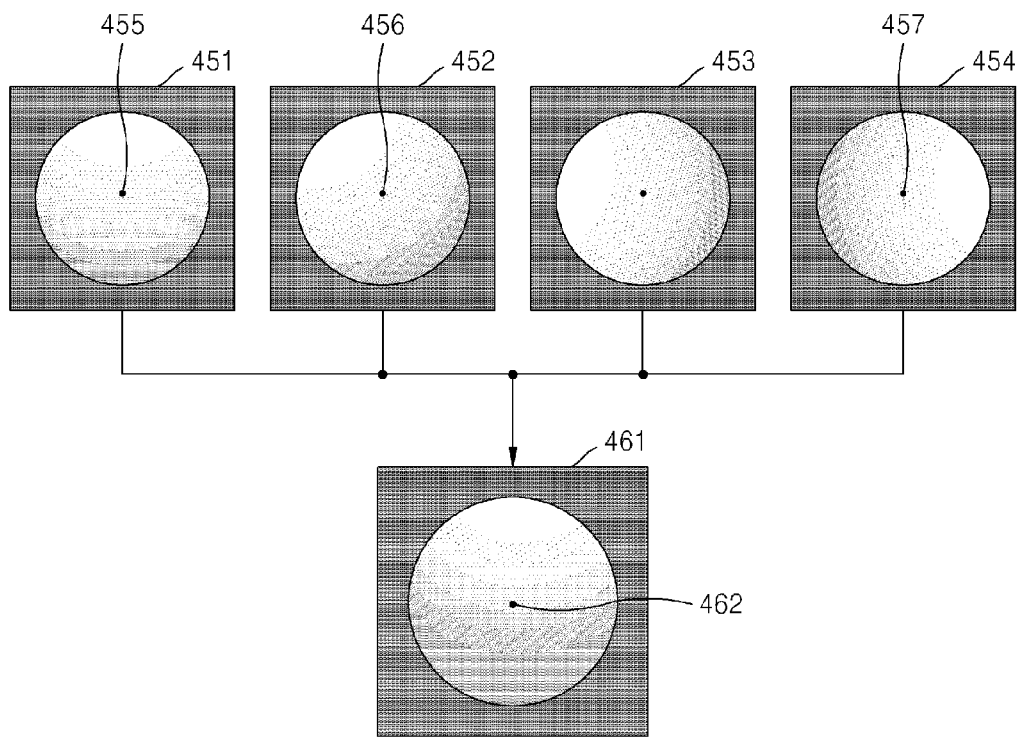
FIG. 4 is a diagram which illustrates an MR image generated by the MR image generating apparatus, according to one or more exemplary embodiments.

FIG. 4 is a diagram which illustrates an MR image generated by the MR image generating apparatus, according to one or more exemplary embodiments.

Referring to FIG. 4, first to Nth channel images 451, 452, 453, 454 which are acquired by the converter 350 and an MR image 461 which is generated by combining the first to Nth channel images 451, 452, 453, 454 in the magnitude image generator 361 are illustrated.

The first channel image 451, the second channel image 452, and the Nth channel image 454 of FIG. 4 respectively correspond to the first channel image 351, the second channel image 352, and the Nth channel image 353 of FIG. 3, and thus, the same descriptions provided with regard to FIG. 3 are not repeated.

Each of the first to Nth channel images 451, 452, 453, 454 includes image data in the frequency domain, and thus becomes a complex image. Therefore, each of the first to Nth channel images 451, 452, 453, 454 includes the magnitude information and the phase information.

The first phase information acquirer 371 acquires a respective phase value in which corresponds to each of the first to Nth channel images 451, 452, 453, 454. The acquired phase value is first phase information.

In detail, the first phase information includes a respective phase value of a center pixel in each of the first to Nth channel images 451, 452, 453, 454 that are each image data.

Referring to FIG. 4, a phase value at a (0, 0) pixel point 455 that is a center pixel of the first channel image 451 is first phase information which corresponds to the first channel, and a phase value at a (0, 0) pixel point 456 that is a center pixel of the second channel image 452 is first phase information corresponds to the second channel. A phase value at a (0, 0) pixel point 457 that is a center pixel of the Nth channel image 454 is first phase information which corresponds to the Nth channel. The first phase information will be described in detail with reference to FIG. 5. Also, a phase value of an MR image 461 may be a phase value at a (0, 0) pixel point 462 that is a center pixel.

Figure 5A:
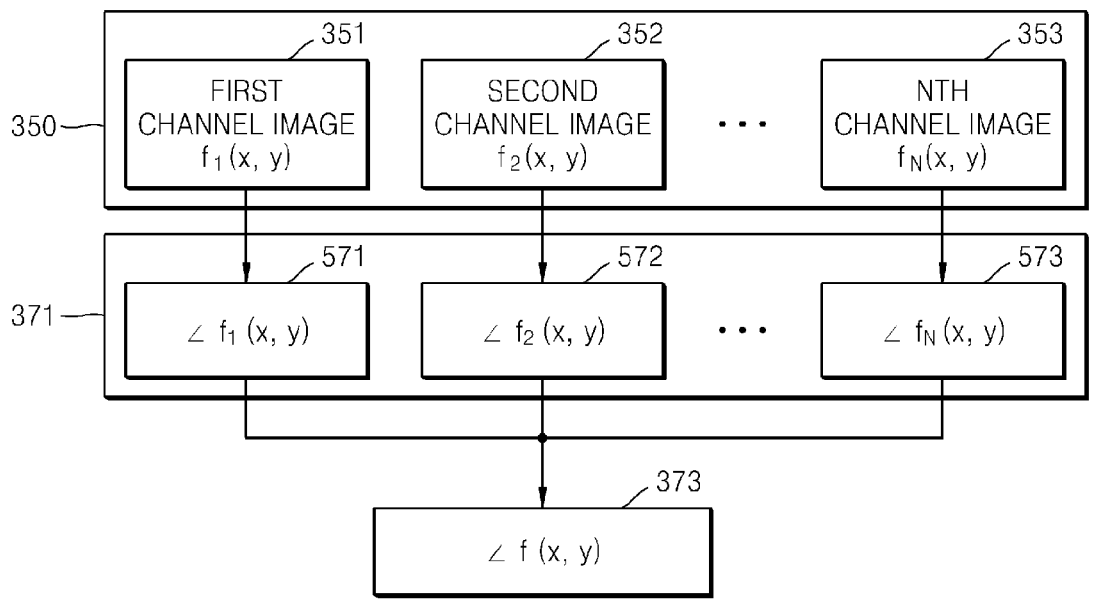
FIGS. 5A and 5B include diagrams which illustrate first phase information generated by the MR image generating apparatus, according to one or more exemplary embodiments.
Figure 5B:
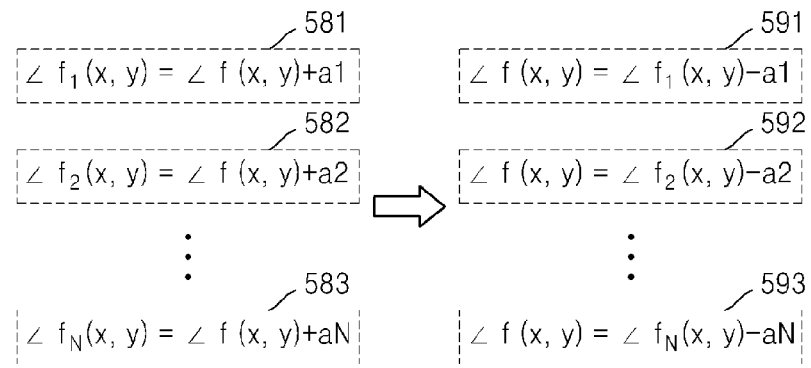

FIGS. 5A and 5B include diagrams which illustrate first phase information generated by the MR image generating apparatus 300, according to one or more exemplary embodiments.

Referring to FIG. 5A, the first phase information acquirer 371 acquires N number of phase values 571, 572, . . . 573 which respectively correspond to the N channels in the respective first to Nth channel images 351, 352, . . . 353 generated by the converter 350. In detail, when the first channel image 351 is $f_1(x, y)$, the phase value of the first channel image 351 is $\angle f_1(x, y)$ 571. When the second channel image 352 is $f_2(x, y)$, the phase value of the second channel image 352 is $\angle f_2(x, y)$ 572. When the Nth channel image 353 is $f_N(x, y)$, the phase value of the Nth channel image 353 is $\angle f_N(x, y)$ 573.

The final phase acquirer 373 may acquire, as phase information of an MR image, an average value "$\angle f(x, y)$" 373 of N pieces of first phase information which respectively correspond to the N channels.

Referring to FIG. 5B, the average value "$\angle f(x, y)$" 373 of the first phase information and a phase value (for example, $\angle f_1(x, y)$ that is the phase value of the first channel image 351) for each channel has a correlation which is expressible as equation 581.

In detail, referring to equation 581, $\angle f_1(x, y)$ 571 that is the phase value of the first channel image 351 has a difference which is equal to a certain value "a1" with $\angle f(x, y)$ that is the average value of the first phase information. Therefore, a phase value of a certain channel image may be expressed by adding a certain offset value to ∠f(x, y) that is the average value of the first phase information.

Moreover, equation 581 may be converted into equation 591. Referring to equation 591, ∠f(x, y) that is the average value of the first phase information may be expressed by subtracting the certain value "a1" from ∠f$_1$(x, y) 571 that is the phase value of the first channel image 351.

Moreover, similarly to equations 581 and 591, ∠f$_2$(x, y) 572 that is a phase value of the second channel image 352 may be expressed as equation 582, and ∠f$_N$(x, y) 573 that is a phase value of the Nth channel image 353 may be expressed as equation 583. Also, equation 582 may be converted into equation 592, and equation 583 may be converted into equation 593.

Moreover, "∠f(x, y)=∠f$_1$(x, y)−a1=∠f$_2$(x, y)−a2= . . . =∠f$_N$(x, y)−aN" may be expressed by combining equations 591, 592, . . . 593.

Moreover, a1 to aN (each of which is a constant) that are respective phase differences between the first phase information for each channel and the phase information "∠f$_1$(x, y)" of the MR image may be calculated by comparing a respective phase value of a certain pixel, included in each channel image, and a respective phase value of a pixel which corresponds to the certain pixel on the other channel.

For example, when the first channel coil that is a first-order coil is a reference, it is assumed that the phase value 571 of the first channel image 351 corresponding to the first channel coil is the phase information "∠f(x, y)" of the MR image, and it is assumed that a phase value of each channel image is a phase value of a center pixel. In this case, a correlation "∠f(0, 0)=∠f$_1$(0, 0)=∠f$_2$(0, 0)−a2= . . . =∠f$_N$(0, 0)−aN" is formed. Therefore, a1 may be calculated as a value of 0, and ∠f(0, 0), ∠f$_1$(0, 0), . . . , ∠Lf$_2$(0, 0) are phase values which are respectively extracted from center pixels of the first to Nth channel images 351 to 353 that are complex images. In this aspect, such phase values are acquired by the first phase information acquirer 371. Accordingly, by applying the acquired ∠f(0, 0), ∠f$_1$(0, 0), . . . , ∠f$_2$(0, 0) to the correlation "∠f(0, 0)=∠f$_1$(0, 0)=∠f$_2$(0, 0)−a2= . . . =∠f$_N$(0, 0)−aN", a1 may be calculated as 0 (i.e., a1=0), and each of a2 to aN may be calculated as a constant.

Therefore, by calculating the constants, the phase information "∠f(x, y)" of the MR image may be calculated as an average value of "∠f$_1$(x, y)−a1", "Lf$_2$(x, y)−a2", . . . , "∠f$_N$(x, y)−aN" which are respectively expressed as equations 591, 592, . . . 593. In detail, the phase information "∠f(x, y)" of the MR image may be calculated as an average value of "∠f$_1$(0, 0)−a1", "∠f$_2$(0, 0)−a2", . . . , "∠f$_N$(0, 0)−aN".

The second phase information acquirer 372 acquires a phase value in each of the pieces of channel total data 341, 342, . . . 343 that are the K-space completion data. Here, a phase value of the K-space completion data is referred to as the second phase information.

In detail, the second phase information may include a phase value at a point in which a signal value of each of the pieces of channel total data 341, 342, . . . 343 (which are the K-space completion data) becomes the respective maximum value. Here, the point in which the signal value becomes the respective maximum value may be a direct (DC) point in the K-space completion data. Also, the direct point in the K-space completion data may be a (0, 0) pixel point that is a center pixel.

Figures 6A, 6B:
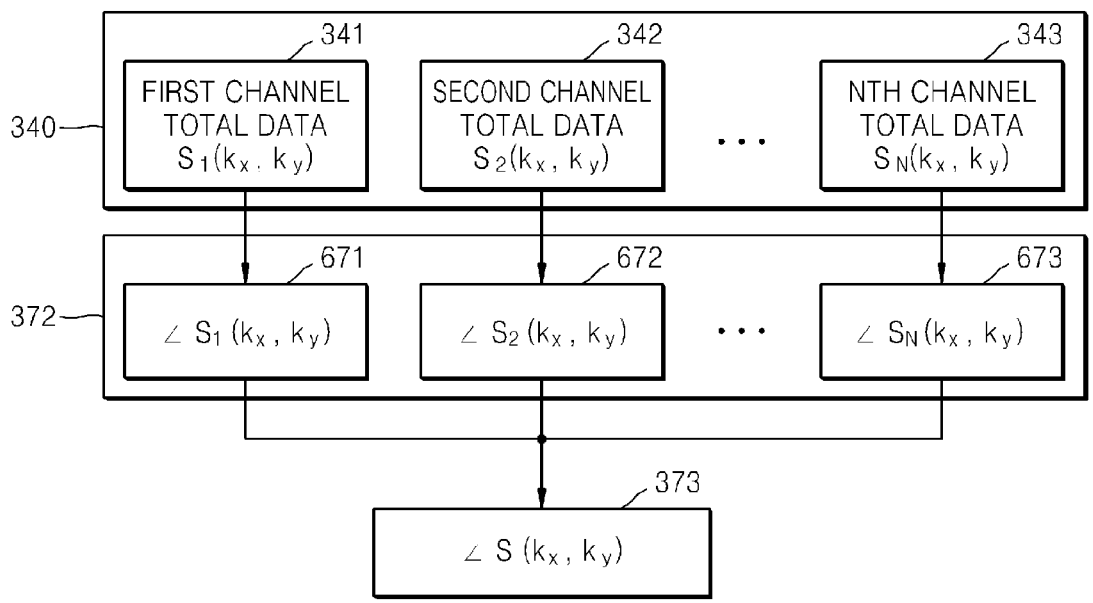
FIGS. 6A and 6B include diagrams which illustrate second phase information generated by the MR image generating apparatus, according to one or more exemplary embodiments.

FIGS. 6A and 6B include diagrams which illustrate second phase information generated by the MR image generating apparatus, according to one or more exemplary embodiments.

Referring to FIG. 6A, the second phase information acquirer 372 acquires N number of phase values 671, 672, . . . 673 which respectively correspond to the N channels in the respective first to Nth channel total data 341, 342, . . . 343 generated by the K-space completion data acquirer 340. In detail, when the first channel total data 341 that is the K-space completion data corresponding to the first channel is S$_1$(K$_x$, K$_y$), the phase value of the first channel total data 341 is ∠S$_1$(K$_x$, K$_y$) 671. When the second channel total data 342 is S$_2$(K$_x$, K$_y$), the phase value of the second channel total data 342 is ∠S$_2$(K$_x$, K$_y$) 672. When the Nth channel total data 343 is S$_N$(K$_x$, K$_y$), the phase value of the Nth channel total data 343 is ∠S$_N$(K$_x$, K$_y$) 673.

The final phase acquirer 373 may acquire, as phase information of an MR image, an average value "∠S(K$_x$, K$_y$)" of N pieces of second phase information which respectively corresponds to the N channels. In detail, when a signal-to-noise ratio (SNR) is low in an image which is acquired by the channel coils included in the RF multi-coil, the final phase acquirer 373 may acquire an average value of the second phase information as the phase information of the MR image.

For example, when a size of each of the channel coils included in the RF multi-coil is relatively small, a portion which is relatively close to a surface of each coil receives an RF signal well, but a portion which is relatively far away from the surface of each coil cannot sufficiently acquire the RF signal. Due to this, an image signal value of a center pixel is insufficient, and thus, an SNR in the center pixel is reduced. In this case, the final phase acquirer 373 may acquire the average value of the second phase information as the phase information of the MR image.

In detail, when the SNR in the center pixel decreases, a size of each dome coil included in a helmet coil for photographing a head is sometimes reduced, and a corresponding size of each of the coils included in the RF multi-coil is sometimes reduced. Therefore, when performing imaging on an MR image by using the RF multi-coil having an unusual geometry like the helmet coil (particularly, the dome coils), the phase information of the MR image may be acquired by using the second phase information.

Referring to FIG. 6B, the average value "∠S(K$_x$, K$_y$)" of the second phase information and a phase value (for example, ∠S$_1$(K$_x$, K$_y$) that is the phase value of the first channel total data) for each channel has a correlation which is expressible as an equation 681.

Similarly to equations 581, 582, . . . 583 described above with reference to FIG. 5B, in each of equations 681, 682, . . . 683 illustrated in FIG. 6B, a phase value of a certain channel total data may be expressed by adding a certain offset value "b1", "b2", or "b3" to ∠S(K$_x$, K$_y$) that is the average value of the second phase information.

Moreover, equation 681 may be converted into equation 691. Therefore, similarly to equations 591, 592, . . . 593 described above with reference to FIG. 5B, in each of equations 691, 692, . . . 693 illustrated in FIG. 6 (*b*), ∠S(K$_x$, K$_y$) that is the phase value of the second channel image may be expressed by subtracting the certain offset value "b1", "b2", or "b3" from a phase value of certain channel total data.

Therefore, in the same way as that of FIGS. 5A and 5B, b1 may be calculated as 0 (i.e., b1=0), and each of b2 to bN may be calculated as a constant. By calculating the constants, an average value of "∠S$_1$(Kx, Ky)−b1", "∠S$_2$(Kx,Ky)−b2", . . . , "∠S$_N$(Kx,Ky)−bN" may be calculated. In detail, ∠S(0, 0) that is an average value of "∠S$_1$(0, 0)−b1", "∠S$_2$(0, 0)−b2", . . . , "∠S$_N$(0, 0)−bN" may be calculated as a phase value of the MR image.

The final phase acquirer 373 may selectively acquire the first phase information and/or the second phase information for each channel coil, and calculate an average value of a plurality of pieces of acquired first phase information or second phase information in order to calculate a phase value of a final MR image.

In detail, the final phase acquirer 373 acquires the second phase information on a channel in which an SNR in a center region of image data is equal to or less than a predetermined value, for example, the first channel image 351, and acquires the first phase information on a channel in which the SNR in a center region of image data is greater than the predetermined value, for example, the second channel image 352. An average value of the acquired first phase information and the acquired second phase information by channel may be acquired as the phase information of the MR image. The predetermined value may be variably set, depending on a product specification of the MR image generating apparatus 300 and a desired image quality.

For example, in a helmet coil for capturing an MR image of a head, a size of each coil included in the helmet coil is relatively small, an upper portion of the helmet coil has a dome structure, and a lower portion of the helmet coil has a cylindrical structure. In a dome coil corresponding to the upper portion of the helmet coil, coils corresponding to respective channels have a small size and an unusual geometry, and an SNR in a center region of an image which is acquired in correspondence with each of the coils is relatively low. Also, in a cylindrical coil corresponding to the lower portion of the helmet coil, an SNR in a center region of an image which is acquired in correspondence with the cylindrical coil is relatively high. Therefore, in the helmet coil, the second phase information may be acquired in channel coils which are disposed at the dome coil side, the first phase information may be acquired in channel coils which are disposed at the cylindrical coil side, and a phase of the MR image may be calculated by averaging the acquired first phase information and the acquired second phase information.

Figure 7:
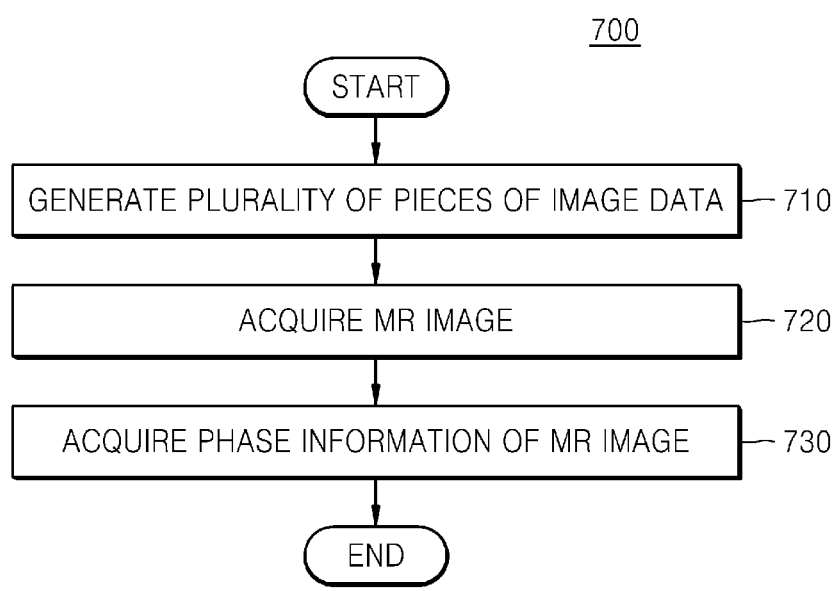
FIG. 7 is a flowchart of an MR image generating method, according to an exemplary embodiment.

FIG. 7 is a flowchart of an MR image generating method 700, according to an exemplary embodiment. The MR image generating method 700 of FIG. 7 includes the detailed operation and structural feature of the MR image generating apparatus 200 or 300 according to one or more exemplary embodiments as described above with reference to FIGS. 1 to 6. Therefore, the same descriptions provided with regard to FIGS. 1 to 6 are not repeated. Hereinafter, the MR image generating method 700 according to an exemplary embodiment will be described with reference to the MR image generating apparatus 200 according to an exemplary embodiment.

The MR image generating method 700 is a method that acquires an MR image by using an RF multi-coil which includes a plurality of channel coils. Here, the plurality of channel coils are N number of channel coils which are included in the RF multi-coil (which is the above-described RF coil 26) and which respectively correspond to first to Nth channels.

In operation 710, the MR image generating method 700 generates a plurality of pieces of K-space completion data which respectively correspond to the plurality of channel coils, and converts the plurality of pieces of K-space completion data to a frequency domain in order to generate a plurality of pieces of image data. Operation 710 may be performed by the image processor 220.

In operation 720, the MR image generating method 700 combines the plurality of pieces of image data (which are generated in operation 710) in order to acquire an MR image. Operation 720 may be performed by the image processor 220.

In operation 730, the MR image generating method 700 acquires phase information which relates to the MR image based on at least one of a plurality of pieces of first phase information, which is channel-specific phase information which corresponds to and which is acquired from the plurality of pieces of image data, and a plurality of pieces of second phase information, which is channel-specific phase information which corresponds to and which is acquired from the plurality of pieces of K-space completion data. Operation 730 may be performed by the phase information acquirer 230.

Moreover, the MR image generating method 700 according to an exemplary embodiment acquires magnitude information and phase information of the MR image, and thus may be applied to an imaging technique which uses phase information, such as, for example, a PCI technique and an SWI technique.

A method for acquiring phase information which relates to a phase contrast image (PCI), according to an exemplary embodiment, is a method that acquires phase information for generating a PCI. The method for acquiring phase information which relates to a PCI includes an operation that generates a plurality of pieces of K-space completion data which respectively correspond to a plurality of channel coils, and converts the plurality of pieces of K-space completion data to a frequency domain in order to generate a plurality of pieces of image data. Furthermore, the method for acquiring phase information which relates to a PCI includes an operation that acquires phase information relating to the PCI based on at least one of a plurality of pieces of first phase information, which is channel-specific phase information which corresponds to and is acquired from the plurality of pieces of image data, and a plurality of pieces of second phase information, which is channel-specific phase information which corresponds to and is acquired from the plurality of pieces of K-space completion data.

A method for acquiring phase information of a susceptibility weighed image (SWI), according to an exemplary embodiment, is a method that acquires phase information for generating an SWI. The method for acquiring phase information which relates to an SWI generates a plurality of pieces of K-space completion data which respectively correspond to a plurality of channel coils, and converts the plurality of pieces of K-space completion data to a frequency domain in order to generate a plurality of pieces of image data. Furthermore, the method for acquiring phase information which relates to an SWI acquires phase information relating to the SWI based on at least one of a plurality of pieces of first phase information, which is channel-specific phase information which corresponds to and is acquired from the plurality of pieces of image data, and a plurality of pieces of second phase information, which is channel-specific phase information which corresponds to and is acquired from the plurality of pieces of K-space completion data.

The method for acquiring phase information which relates to a PCI and the method for acquiring phase information which relates to an SWI, according to an exemplary embodiment, have the same technical spirit as that of the above-described MR image generating method 700 of FIG. 7, and thus, their detailed descriptions are not provided.

FIG. 8 is a flowchart of an MR image generating method 800, according to another exemplary embodiment. The MR image generating method 800 of FIG. 8 includes the detailed operation and structural feature of the MR image generating apparatus 200 or 300 according to one or more exemplary embodiments described above with reference to FIGS. 1 to 6.

Therefore, the same descriptions provided with regard to FIGS. 1 to 6 are not repeated. Also, operations 830, 840, and 850 of the MR image generating method 800 respectively correspond to operations 710, 720, and 730 of the MR image generating method 700, and thus, the same descriptions provided with regard to FIG. 7 are not provided.

Hereinafter, the MR image generating method 800 according to another exemplary embodiment will be described with reference to the MR image generating apparatus 300 of FIG. 3.

Referring to FIG. 8, in operation 810, the MR image generating method 800 acquires a plurality of pieces of K-space raw data in a plurality of channel coils. Here, the plurality of pieces of K-space raw data may include a plurality of pieces of under-sampled K-space data which are respectively acquired by the plurality of channel coils, and which respectively correspond to the first to Nth channel data 331, 332, ... 333 of FIG. 3. Operation 810 may be performed by the K-space raw data acquirer 330.

In operation 820, the MR image generating method 800 performs auto-calibration on the acquired plurality of pieces of K-space raw data in order to acquire a plurality of pieces of K-space completion data. Operation 820 may be performed by the K-space completion data acquirer 340. The plurality of pieces of K-space completion data respectively correspond to the first to Nth channel total data 341, 342, ... 343 of FIG. 3.

In particular, operation 820 sets an auto-calibration line data which is included in the pieces of under-sampled K-space data. Alternatively, the MR image generating apparatus 300 further acquires auto-calibration (ACS) line data in addition to the acquired line data in the pieces of K-space raw data. In addition, operation 820 estimates line data which is not acquired in the plurality of pieces of under-sampled K-space data, based on the acquired line data and the auto-calibration line data included in the pieces of under-sampled K-space data. Furthermore, operation 820 acquires the K-space completion data based on the estimated line data and the pieces of under-sampled K-space data.

In operation 830, the MR image generating method 800 performs an FFT on the generated plurality of pieces of K-space completion data in order to generate a plurality of pieces of image data. Operation 830 may be performed by the converter 350. In this operation, the plurality of pieces of image data respectively correspond to the first to Nth channel images 351, 352, ... 353 of FIG. 3.

In operation 840, the MR image generating method 800 combines the plurality of pieces of image data (which are generated in operation 830) in order to acquire an MR image. Operation 840 may be performed by the image acquirer 360. In detail, operation 840 may calculate a sum of square values which relate to the plurality of pieces of image data in order to acquire the MR image. The MR image generated in operation 840 may be a magnitude image composed of magnitude information. Further, the image acquirer 360 may combine the magnitude image with the phase information generated by the phase information acquirer 370 in order to generate a final MR image. Therefore, the final MR image is a complex image which includes the magnitude information and the phase information.

In operation 850, the MR image generating method 800 acquires phase information which relates to the MR image based on at least one of a plurality of pieces of first phase information, which is channel-specific phase information which corresponds to and is acquired from the plurality of pieces of image data, and a plurality of pieces of second phase information, which is channel-specific phase information which corresponds to and is acquired from the plurality of pieces of K-space completion data. Operation 850 may be performed by the phase information acquirer 370.

In detail, operation 850 includes operation 851 in which the first phase information is acquired, operation 852 in which the second phase information is acquired, and operation 853 in which a phase of the MR image is acquired based on at least one of the acquired first phase information and the acquired second phase information. Here, operation 851 may be performed by the first phase information acquirer 371, and operation 852 may be performed by the second phase information acquirer 372. Operation 853 may be performed by the final phase acquirer 373.

In particular, the first phase information may include a respective phase value of a center pixel in a corresponding one of the plurality of pieces of image data which are generated in operation 830. The second phase information may include a respective phase value at a point in which a signal value of a corresponding one of the plurality of pieces of K-space completion data (which are acquired in operation 820) becomes the maximum value.

As described above, according to the one or more of the above-described exemplary embodiments, by using the GRAPPA technique, a phase value of an MR image may be acquired by performing image processing in parallel for each of a plurality of channels for generating the MR image. Therefore, by performing the image processing in parallel, an image processing speed increases, and a potential limitation of the GRAPPA technique relating to an MR image not including phase information is overcome, thus accurately and easily facilitating an acquisition of a phase value of an MR image.

The above-described embodiments may be written as computer programs and may be implemented in general-use digital computers that execute the programs using transitory and/or non-transitory computer-readable recording media.

Examples of the computer-readable recording medium include magnetic storage media (e.g., ROM, floppy disks, hard disks, etc.) and optical recording media (e.g., CD-ROMs or DVDs).

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A method for imaging a magnetic resonance (MR) image by using a radio frequency (RF) multi-coil which includes a plurality of channel coils, the MR image generating method comprising:

generating a plurality of pieces of K-space completion data which respectively correspond to the plurality of channel coils, and converting the plurality of pieces of K-space completion data to a frequency domain in order to generate a plurality of pieces of image data;

acquiring the plurality of pieces of image data in order to acquire the MR image; and acquiring phase information which relates to the MR image based on at least one of first phase information, which is channel-specific phase information for a plurality of channels and acquired from the plurality of pieces of image data, and second phase information which is channel-specific phase information for a plurality of channels and acquired from the plurality of pieces of K-space completion data, wherein the generating a plurality of pieces of image data comprises, acquiring a plurality of pieces of K-space raw data which respectively correspond to the plurality of channel coils, and acquiring the plurality of pieces of K-space completion data by performing an auto-calibration on each of the acquired plurality of pieces of K-space raw data.

2. The MR image generating method of claim 1, wherein the first phase information comprises a phase value of a center pixel in the corresponding one of the plurality of pieces of image data.

3. The MR image generating method of claim 2, wherein the second phase information comprises a phase value at a point in which a signal value of the corresponding one of the plurality of pieces of K-space completion data becomes a maximum value.

4. The MR image generating method of claim 2, wherein the acquiring the phase information comprises acquiring, as the phase information of the MR image, an average value of the plurality of pieces of first phase information respectively corresponding to the plurality of channel coils.

5. The MR image generating method of claim 3, wherein the acquiring the phase information comprises acquiring, as the phase information of the MR image, an average value of the plurality of pieces of second phase information respectively corresponding to the plurality of channel coils when the RF multi-coil is a dome type.

6. The MR image generating method of claim 3, wherein the acquiring the phase information comprises:
acquiring the second phase information on a first channel in which a signal-to-noise ratio (SNR) in a center region of the image data is equal to or less than a predetermined value;
acquiring the first phase information on a second channel in which the SNR in the center region of the image data is greater than the predetermined value; and
acquiring the phase information which relates to the MR image based on the acquired first phase information and the acquired second phase information.

7. The MR image generating method of claim 1, wherein the generating the plurality of pieces of image data comprises:
generating the plurality of pieces of image data by performing a fast Fourier transform (FFT) on the generated plurality of pieces of K-space completion data.

8. The MR image generating method of claim 7, wherein, the plurality of pieces of K-space raw data are a plurality of pieces of under-sampled K-space data which are respectively acquired by the plurality of channel coils, and
the acquiring of the plurality of pieces of K-space completion data comprises:
estimating line data which is not acquired in the pieces of under-sampled K-space data, based on acquired line data and auto-calibration line data which are included in the pieces of under-sampled K-space data; and
acquiring the K-space completion data based on the estimated line data and the pieces of under-sampled K-space data.

9. The MR image generating method of claim 1, wherein the acquiring the MR image comprises acquiring the MR image by calculating a sum of square values of the plurality of pieces of image data to acquire the MR image.

10. A method for acquiring phase information which relates to a phase contrast image (PCI), the method comprising:
generating a plurality of pieces of K-space completion data which respectively correspond to a plurality of channel coils, and generating a plurality of pieces of image data by converting the plurality of pieces of K-space completion data to a frequency domain; and
acquiring the phase information which relates to the PCI based on at least one of first phase information, which is channel-specific phase information for a plurality of channels and acquired from each of the plurality of pieces of image data, and second phase information which is channel-specific phase information for a plurality of channels and acquired from each of the plurality of pieces of K-space completion data,
wherein the generating a plurality of pieces of image data comprises,
acquiring a plurality of pieces of K-space raw data for each of the plurality of channel coils, and
acquiring the plurality of pieces of K-space completion data by performing an auto-Calibration on each of the acquired plurality of pieces of K-space raw data.

11. A method for imaging a susceptibility weighted image (SWI) by using a radio frequency (RF) multi-coil which includes a plurality of channel coils, the method comprising:
generating a plurality of pieces of K-space completion data which respectively correspond to a plurality of channel coils, and generating a plurality of pieces of image data by converting the plurality of pieces of K-space completion data in a frequency domain in order to generate a plurality of pieces of image data; and
acquiring the phase information which relates to the SWI based on at least one of first phase information, which is channel-specific phase information for a plurality of channels and acquired from each of the plurality of pieces of image data, and a second phase information which is channel-specific phase information for a plurality of channels and acquired from each of the plurality of pieces of K-space completion data,
wherein the generating a plurality of pieces of image data comprises,
acquiring a plurality of pieces of K-space raw data for each of the plurality of channel coils, and
acquiring the plurality of pieces of K-space completion data by performing an auto-calibration on each of the acquired plurality of pieces of K-space raw data.

12. A apparatus for imaging magnetic image (MR) image by using a radio frequency (RF) multi-coil which includes a plurality of channel coils, the MR image generating apparatus comprising:
an image processor configured to generate a plurality of pieces of K-space completion data which correspond to the plurality of channel coils, to generate a plurality of pieces of image data by converting the plurality of pieces of K-space completion data in a frequency domain, and to acquire the MR image by combining the generated plurality of pieces of image data; and
a phase information acquirer configured to acquire phase information of the MR image based on at least one of first phase information, which is channel-specific phase information for a plurality of channels and acquired from each of the plurality of pieces of image data, and second phase information, which is channel-specific phase information for the plurality of channels and acquired from each of the plurality of pieces of K-space completion data, wherein the image processor is further configured to:
acquire K-space raw data for each of the plurality of channel coils, and
acquire the plurality of pieces of K-space completion data by performing an auto-calibration on each of the acquired plurality of pieces of K-space raw data.

13. The MR image generating apparatus of claim 12, wherein the first phase information comprises a phase value of a center pixel in each of the plurality of pieces of image data.

14. The MR image generating apparatus of claim 13, wherein the second phase information comprises a phase value at a point in which a signal value of each of the plurality of pieces of K-space completion data becomes a maximum value.

15. The MR image generating apparatus of claim 13, wherein the phase information acquirer is further configured to acquire, as the phase information of the MR image, an average value of the plurality of pieces of first phase information respectively corresponding to the plurality of channel coils.

16. The MR image generating apparatus of claim 14, wherein when the RF multi-coil has a dome type, the phase information acquirer is further configured to acquire, as the phase information of the MR image, an average value of the plurality of pieces of second phase information respectively corresponding to the plurality of channel coils.

17. The MR image generating apparatus of claim 14, wherein the phase information acquirer is further configured to acquire the second phase information on a channel in which a signal-to-noise ratio (SNR) in a center region of the image data is equal to or less than a predetermined value, to acquire the first phase information on a channel in which the SNR in the center region of the image data is greater than the predetermined value, and to acquire the phase information which relates to the MR image based on the acquired first phase information and the acquired second phase information.

18. The MR image generating apparatus of claim 12, wherein the image processor comprises:
a converter configured to generate the plurality of pieces of image data by performing a fast Fourier transform (FFT) on the plurality of pieces of K-space completion data; and
an image acquirer configured to acquire the MR image by calculating a sum of square values of the plurality of pieces of image data.

19. The MR image generating apparatus of claim 17, wherein,
the plurality of pieces of K-space raw data are a plurality of pieces of under-sampled K-space data which are respectively acquired by the plurality of channel coils, and
the K-space data acquirer is further configured to estimate auto-calibration line data based on acquired line data acquired in the pieces of under sampled K-space data, and to estimate line data which is not acquired based on the acquired line data and the auto-calibration line data, and to acquire the K-space completion data based on the estimated line data and the pieces of under-sampled K-space data.

* * * * *